United States Patent [19]

Enlow et al.

[11] Patent Number: 5,342,978

[45] Date of Patent: Aug. 30, 1994

[54] ORGANIC PHOSPHITE ESTER COMPOSITIONS CONTAINING HINDERED PIPERDINYL LIGHT STABILIZERS

[75] Inventors: William P. Enlow, Belpre, Ohio; Leo L. Valdiserri, Roswell, Ga.

[73] Assignee: General Electric Company, Pittsfield, Mass.

[21] Appl. No.: 66,695

[22] Filed: May 24, 1993

[51] Int. Cl.$^5$ .................................................. C07F 9/02
[52] U.S. Cl. ........................................ 554/78; 558/71; 558/70; 558/218
[58] Field of Search ................................ 554/78; 558/71

[56] References Cited

U.S. PATENT DOCUMENTS

| | | | |
|---|---|---|---|
| 2,114,866 | 4/1938 | Vaughn | 556/466 |
| 3,553,298 | 1/1971 | Hodan et al. | 558/71 |
| 3,640,928 | 2/1972 | Murayama et al. | 524/99 |
| 3,787,537 | 1/1974 | DeMarco | 558/71 |
| 4,111,901 | 9/1978 | Hechenbleiker | 524/104 |
| 4,116,926 | 9/1978 | York | 524/120 |
| 4,206,111 | 6/1980 | Valdiserri et al. | 524/91 |
| 4,302,383 | 11/1981 | Valdiserri et al. | 524/105 |
| 4,331,585 | 3/1982 | Valdiserri et al. | 524/103 |
| 4,767,834 | 8/1988 | Leistner et al. | 526/265 |

FOREIGN PATENT DOCUMENTS 84114400 11/1984 European Pat. Off. .

OTHER PUBLICATIONS

*Technical Aspects of Light Stabilizers*, Light Stabilizers for Thermoplastic, pp. 152–157, R. Gachter et al., 1985.

*Primary Examiner*—Paul J. Killos
*Assistant Examiner*—Dwayne C. Jones

[57] ABSTRACT

Hydrolytically stabilized phosphite compositions are provided. The compositions contain an organic phosphite ester antioxidant and a hindered piperidinyl light stabilizer. The hindered piperidinyl component is not only a light stabilizer but also functions to hydrolitically stabilize the organic phosphite antioxidant. The compositions are useful as stabilizer additives to polymeric compositions.

9 Claims, No Drawings

ORGANIC PHOSPHITE ESTER COMPOSITIONS CONTAINING HINDERED PIPERDINYL LIGHT STABILIZERS

BACKGROUND OF THE INVENTION

1. Field of the Invention

The present invention relates to organic phosphite ester compositions, and more particularly relates to organic phosphite ester compositions hydrolytically stabilized by a hindered piperidinyl light stabilizer.

2. Description of the Related Art

The purpose of stabilizers for polymers is to prevent deterioration of the polymers during processing at high temperatures, and also to permit manufacture of products with increased intrinsic quality because of the enhancement of their resistance to thermal and light degradation during use. In addition, because of the ability of these products to withstand more rigorous conditions, their versatility is increased and new areas of application are thereby opened.

An important class of polymer stabilizers are the organic phosphites. They include, as a specially useful group, the dialkylpentaerythritol diphosphites and diarylpentaerythritol diphosphites. They are used widely in the stabilization of vinyl chloride polymers, polyolefins and styrene polymers such as ABS. The dialkylpentaerythritol diphosphites and diarylpentaerythritol diphosphites have the structural formula:

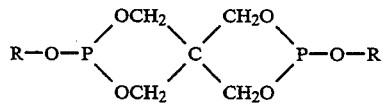

where each R is independently selected from alykyl or aryl groups.

Despite such wide usage, however, these types of stabilizers have not been entirely satisfactory, because of their own slight hydrolytic instability on storage. They tend to absorb moisture from a moist environment and their effectiveness as stabilizers for polymers seems to decline in direct proportion to the amount of water absorbed.

This disadvantage can be avoided by taking care to store and transport the stabilizer only in a dry atmosphere. Once incorporated in a polymer composition, lesser problems are presented apparently because of the essentially anhydrous condition of such polymer compositions.

Obviously, though, elimination or a least amelioration of the problem is desirable. A moisture-insensitive phosphite stabilizer will preclude the many inconveniences and expense associated with having to maintain an anhydrous environment, prior to incorporation into polymer.

U.S. Pat. No. 3,553,298 (Hodan) shows the stabilization of phosphite esters broadly by using any of several classes of amines including triisopropanol amine. See column 2, line 24 and Examples I-VI.

M. C. Imaev, Zhurnal Obshchel Khim. 31, 1767-70 (1961) shows the stabilization of lower trialkyl phosphites with organic and inorganic bases. The organic bases shown include pyridine, triethyl amine and dimethyl aniline.

U.S. Pat. No. 2,114,866 (Vaughn) shows the stabilization of esters of inorganic esters with an amine. While Vaughn is interested primarily in organic silicates he does mention also (see page 2, column 2, lines 17-22) borates, phosphates, "symmetrical" phosphites, arsenates and symmetrical arsenites.

U.S. Pat. No. 3,787,537 (Marcq) discloses a class of phosphite esters which are said to be stable to hydrolysis. Marcq refers also (see column 2, lines 9-10) to the stabilization of previously known phosphites by "a small quantity of a heavy amine, usually triisopropanolamine (French Pat. No. 1,582,387)". The cited French patent is a counterpart of the above Hodan et al U.S. patent.

As mentioned above, ultraviolet light has a degradative effect on olefin polymers, the severity of which is dependent on the particular polymer and the geographical location of exposure. The degradation may take the form of discoloration, loss of tensile and impact strength, distortion of initial flexibility, dimensional change, surface craze, cracking, powdering or increased electrical conductivity. All of these effects may result from the breaking of carbon-to-carbon bonds in the polymer or from crosslinking of the polymer.

It is well known that the addition of certain materials to an olefin polymer will impart a degree of stabilization to that polymer with respect to its resistance to the destructive forces of ultraviolet radiation. Hindered amine light stabilizers are commonly used in many polymers to inhibit polymer degradation which is accelerated by exposure of the polymer to light.

U.S. Pat. No. 3,640,928 (Murayama et al.) which is incorporated herein by reference shows the stabilization of synthetic polymers by the presence therein of certain piperidine compounds wherein the two carbon atoms adjacent to the ring nitrogen each contain two alkyl substituents. The piperidine compounds contain also an oxy substituent in the four-position and, in many instances, two or more piperidine nuclei are joined to one another by means of polyfunctional ether, ester, carbamate, sulfonate, etc. groups.

U.S. Pat. No. 4,302,383 (Valdiserri et al.) which is incorporated herein by reference shows the stabilization of olefin polymer compositions containing stabilizer composition comprising a cyclic hindered amine selected from pyrrolidines and pyrrolines in combination with an organic phosphite ester.

While both phosphites and hindered amines are known additives for stabilizing polymeric compositions, applicant has discovered that combining these phosphite antioxidants and hindered piperidinyl light stabilizers as a nonpolymeric blend composition provides an organic phosphite ester composition that contains a light stabilizer that hydrolytically stabilizes the phosphite ester antioxidant contained therein.

SUMMARY OF THE INVENTION

A composition is provided which contains an organo phosphite ester and a hindered piperidinyl light stabilizer. The hindered piperidinyl light stabilizer improves the hydrolytic stability of the organophosphite ester. The compositions are useful as additives to polymers for the stabilization thereof.

DETAILED DESCRIPTION OF THE INVENTION

The organic phosphite ester of the stabilizer composition preferably is a pentaerythritol diphosphite which in most instances is characterized by a spiro structure, i.e.,

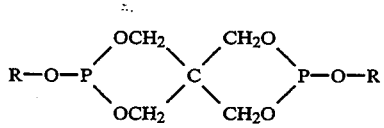

where each R is independently selected from organic radicals. Particularly preferred radicals for each R are alkyl and alkylphenyl. When R is alkyl it should contain 10 to 20 carbon atoms, inclusive, and an especially desirable phosphite is distearyl pentaerythritol diphosphite; when R is alkylphenyl the alkyl substituents should contain 3 to 10 carbon atoms and, preferably, should be tertiary alkyl groups. Tertiarybutyl radicals are especially preferred. The alkylphenyl groups may contain up to three alkyl substituents.

The phosphite esters may be made by a variety of methods. The dialkyl pentaerythritol diphosphites may in general be prepared by transesterification of diphenyl pentaerythritol diphosphite with the appropriate alcohol, e.g., stearyl alcohol or decyl alcohol. Alternatively, the same alcohol can be reacted with dichloro pentaerythritol diphosphite. The di(alkylphenyl) pentaerythritol diphosphite may be prepared similarly, by either of the above methods. Other methods are known and described in the literature.

A large number of organic phosphite ester compounds have been proposed for use as melt flow stabilizers and secondary antioxidants for thermoplastic molding and extrusion compositions. Some of the more effective phosphites are organic phosphite esters having the formula:

$$P-(OR)_3$$

Where each R is independently selected from alkyl, aryl, alkaryl, aralkyl and substituted alkyl, aryl, alkaryl and aralkyl groups.

As set out above, an important class of phosphite esters is based on polyfunctional alcohols such as pentaerythritol and have the formula:

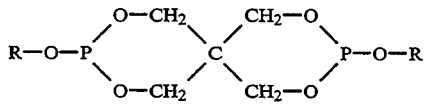

Where each R is independently selected from alkyl, aryl, alkaryl, aralkyl and substituted alkyl, aryl, alkaryl and aralkyl groups. Examples of the latter include distearyl pentaerythritol diphosphite and bis (2,4-di-tert-butyl phenyl) pentaerythritol diphosphite, described, respectively, in U.S. Pat. Nos. 4,064,100 and 4,305,866 which are incorporated herein by reference. The preparation of various trialkyl and trialkenyl phosphites is described in U.S. Pat. No. 3,939,229.

Preferred organic phosphite esters for the compositions of the present invention include trinonylphenyl phosphite, triphenyl phosphite, distearyl pentaerythritol diphosphite, bis(2,4,6-tri-t-butyl phenyl) pentaerythritol diphosphite and bis(2,4-di-t-butyl phenyl) pentaerythritol disphosphite.

The organic phosphite esters as the term is used herein also include phosphites and phosphonites such as triphenyl phosphite, diphenylalkyl phosphites, phenyl-dialkyl phosphites, tris(nonyl-phenyl)phosphite, trilauryl phosphite, trioctadecyl phosphite, distearyl pentaerythritol diphosphite, tris(2,4-di-tert-butylphenyl)-phosphite, diisodecyl pentaerythritol diphosphite, bis(2,4-di-tertbutylphenyl) pentaerythritol diphosphite tristearyl sorbitol triphosphite, tris(2,4-di-t-butyl-phenyl) phosphite, fluorophosphites such as the cyclic fluorophosphite from ethylidene bis(2,4-di-t-butyl-phenol and tetrakis (2,4-di-tert-butylphenyl) 4,4'-biphenylene diphosphonite.

Sterically hindered piperidinyl compounds are sterically hindered amine light stabilizers which include for example bis-(2,2,6,6-tetramethylpiperidinyl)-sebacate, bis-(1,2,2,6,6-pentamethylpiperidinyl)-sebacate, n-butyl-3,5-di-tert-butyl-4-hydroxybenzyl malonic acid bis(1,2,2,6,6-pentamethylpiperidinyl)ester, condensation product of 1-hydroxyethyl-2,2,6,6-tetramethyl-4-hydroxy-piperidine and succinic acid, condensation product of N,N'-(2,2,6,6-tetramethylpiperidinyl)hexamethylendiamine and 4-tert-octylamino-2,6-dichloro-1,3,5-s-triazine, tris-(2,2,6,6-tetramethylpiperidinyl)-nitrilotriacetate, tetrakis-(2,2,6,6-tetramethyl-4-piperidinyl)-1,2,3,4-butane-tetra-carbonic acid, 1,1'(1,2-ethanediyl)-bis-(3,3,5,5-tetramethylpiperazinone).

Suitable hindered piperidinyls include bis(1,2,2,6,6-pentamethyl-4-piperidinyl)-2-N-butyl-2-(3,5-di-tert-butyl-4-hydroxybenzyl) malonate; bis(2,2,6,6-tetramethyl-4-piperidinyl) sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidinyl) hexamethylene diamine.

Preferred hindered piperidinyl light stabilizers for use in the present composition may be represented by the formula:

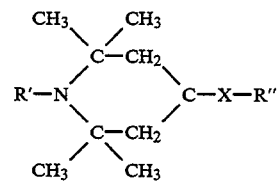

Wherein R" is selected from hydrogen and the group consisting of hydrocarbon radicals; R' is selected from hydrogen, hydroxyl and the group consisting of hydrocarbon radicals; and X is selected from the group consisting of oxygen and nitrogen. Hindered piperidinyl light stabilizers contain the following structural moiety wherein W is selected from the group consisting of alkyl, aryl, or alkylaryl; and R' is selected from hydrogen, hydroxy, alkyl, aryl, or alkylaryl. The hindered piperidinyl preferably has moieties of the formula:

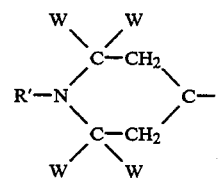

Preferably the stabilizers contain structural moieties selected from:

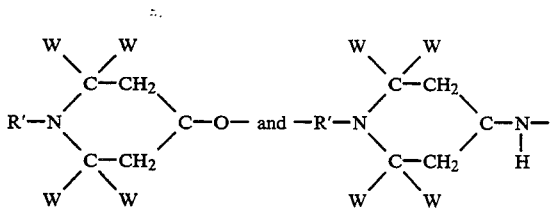

A preferred hindered piperidinyl light stabilizer poly-(6-((1,1,3,3-tetra methylbutyl)-imino)-1,3,5-triazine-2,4-diyl) (2-(2,2,6,6-tetra methyl piperidinyl)-imino-hexamethylene)-(4-(2,2,6,6-tetramethyl piperidinyl-imino) which may be represented by the formula:

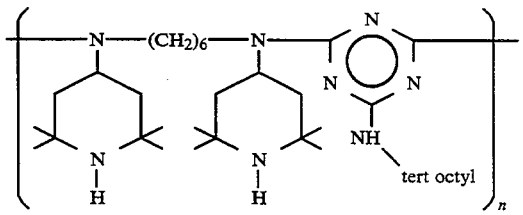

Wherein n is selected from 1 to 50. Another preferred hindered piperidinyl light stabilizer poly-(N-B-hydroxyethyl-2,2,6,6-tetramethyl-4-hydroxypiperidinyl succinate which may be represented by the formula:

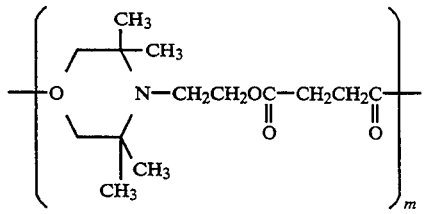

Wherein m is selected from 1 to 50.

Other hindered amines may also be included in or excluded from the present compositions including for example, hindered amines having the structures:

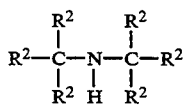

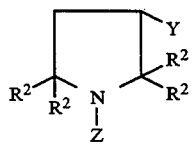

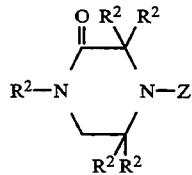

Wherein Z is preferably hydrogen (H), Y is preferably a hydrocarbon group. $R^2$ is preferably an alkyl group.

Hindered amine light stablizers are most easily defined as aliphatic amines or saturated heterocylic amines which have no protons on 2 of the carbons attached to nitrogen. They will form stable nitroxyl radicals.

The hydrolytically stabilized phosphite ester compositions of the present invention may optionally also contain or be free of various conventional additives, such as the following:

Suitable non-phosphite antioxidants include alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(alpha-methylcyclohexyl)-4,6-dimethylphenol, 2,6-di-octadecyl-4-methylphenol, 2,4,6-tricyclohexyphenol, 2,6-di-tert-butyl-4-methoxymethylphenol;

Alkylated hydroquinones, for example, 2,6-di-tert-butyl-4-methoxyphenol, 2,5-di-tert-butylhydroquinone, 2,5-di-tert-amyl-hydroquinone, 2,6-diphenyl-4-octadecyloxyphenol;

Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl-3-methylphenol), 4,4'-thio-bis-(6-tert-butyl-2-methylphenol);

Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(alphamethylcyclohexyl)phenol], 2,2'-methylene-bis-(4-methyl-6-cyclohexylphenol), 2,2'-methylene-bis(6-nonyl-4-methylphenol), 2,2'-methylene-bis-(6-(alpha-methylbenzyl)-4-nonylphenol), 2,2'-methylene-bis-(6-(alpha, alpha-dimethylbenzyl)-4-nonylphenol), 2,2'-methylene-bis-(4,6-di-tertbutylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3-bis-(3'-tert-butyl-4'-hydroxy-phenyl)-butyrate), di-(3-tert-butyl-4-hydroxy-5-methylphenyl)-dicyclopentadiene, di(2-(3'-tert-butyl-2'-hydroxy-5'methyl-benzyl)-6-tert-butyl-4-methylphenyl)-terephthalate;

Benzyl compounds, for example, 1,3,5-tris(3,5-di-tert-butyl-4-hydroxybenzyl)-2, 4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiolterephthalate, 1,3,5-tris(3,5-di-tert-butyl-4-hydroxybenzyl)isocyanurate, 1,3,5-tris-(4-tert-butyl-3-hydroxy-2,6-dimethylbenzyl)isocyanurate, dioctadecyl 3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl)isocyanurate;

Acylaminophenols, for example, 4-hydroxylauric acid anilide, 4-hydroxy-stearic acid anilide, 2,4-bis-octylmercapto-6-(3,5-tert-butyl-4-hydroxyanilino)-s-triazine, octyl-N-(3,5-di-tert-butyl-4-hydroxyphenyl)-carbamate;

Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, di-hydroxyethyl oxalic acid diamide;

Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide;

Esters of beta-(5-tert-butyl-4-hydroxy-3-methylphenyl) propionic acid with mono-or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide;

Amides of beta-(3,5-di-tert-butyl-4-hydroxyphenol)-propionic acid for example, N,N'-di-(3,5-di-tert-butyl-4-hydroxyphenylpropionyl)-hexamethylendiamine, N,N'-di-(3,5-di-tert-butyl-4-hydroxyphenylpropionyl)-trimethylenediamine, N,N'-di-(3,5-di-tert-butyl-4-hydroxyphenylpropionyl)-hydrazine.

The compositions may contain, or be free of, other light stabilizers such as 2-(2'-hydroxyphenyl)-benzotriazoles, for example, the 5'methyl-,3'5'-di-tert-butyl-,5'-tert-butyl-5'(1,1,3,3-tetramethylbutyl)-,5-chloro-3',5'di-tert-butyl-, 5-chloro-3'tert-butyl-5'-methyl-,3'sec-butyl-5'tert-butyl-,4'-octoxy,3',5'-ditert-amyl-, 3',5'-bis-(alpha,alphadimethylbenzyl)-derivatives.

2-Hydroxy-benzophenones, for example, the 4-hydroxy-, 4-methoxy-,4-octoxy,4-decyloxy-,4-dodecyloxy-, 4-benzyloxy,4,2',4'-trihydroxy-and 2'hydroxy-4,4'-dimethoxy derivative.

Esters of substituted and unsubstituted benzoic acids for example, phenyl salicylate, 4-tert-butyl-phenylsalicilate, octylphenyl salicylate, dibenzoylresorcinol, bis-(4-tertbutylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

Acrylates, for example, alpha-cyano-beta, beta-diphenylacrylic acid ethyl ester or isooctyl ester, alpha-carbomethoxy-cinnamic acid methyl ester, alpha-cyano-beta-methyl-p-methoxy-cinnamic acid methyl ester or butyl ester, alphacarbomethoxy-p-methoxy-cinnamic acid methyl ester, N-(beta-carbomethoxy-beta-cyano-vinyl)-2-methyl-indoline.

Nickel compounds, for example, nickel complexes of 2,2'-thio-bis (4-(1,1,1,3-tetramethylbutyl)-phenol), such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert-butylbenzyl-phosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

Oxalic acid diamides, for examples, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5, 4-di-tert-butyloxanilide and mixtures of ortho- and para-methoxy- as well as of o-and p-ethoxy-disubstituted oxanilides.

Other additives may include metal deactivators, for example N,N'-diphenyloxalic acid diamide, N-salicylal-N'-salicyloylhydrazine, N,N'bis-salicyloylhydrazine, N,N'-bis-(3,5-di-tert-butyl-4-hydrophenylpropionyl)-hydrazine, salicyloylamino-1,2,4,-triazole, bis-benzylidenoxalic acid dihydrazide.

Peroxide scavengers, for example, esters of beta-thiodipropionic acid, for example the lauryl, stearyl, myristyl or tridecyl esters, mercaptobenzimidazole or the zinc salt of 2-mercaptobenzimidazole, zinc-dibutyldithiocarbamate, dioctadecyldisulfide, pentaerythritol-tetrakis-(beta-dodecylmercapto)-propionate.

Polyamide stabilizers, for example copper salts in combination with iodides and/or phosphorus compounds and salts of divalent manganese.

Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, Zn stearate, Mg stearate, Na ricinoleate and K palmitate, antimony pyrocatecholate or zinc pyrocatecholate.

Nucleating agents, for example, 4-tert-butylbenzoic acid, adipic acid, diphenylacetic acid.

Fillers and reinforcing agents, for example, calcium carbonate, silicates, glass fibers, asbestos, talc, kaolin, mica, barium sulfate, metal oxides and hydroxides, carbon black and graphite.

The present invention may also be used in conjunction with aminoxy propanoate derivatives such as methyl-3-(N,N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)3(N,N-dibenzylaminoxy)propanoate); octadecyl-3-(N,N-dibenzyl-aminoxy)propanoic acid; tetrakis(N,N-dibenzylaminoxy)ethyl carbonyl oxymethyl)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

Other additives, for example, plasticizers, lubricants, emulsifiers, pigments, optical brighteners, flame-proofing agents, anti-static agents, blowing agents and thiosynergists such as dilaurythiodipropionate or distearylthiodipropionate.

Hindered phenolic antioxidants may also be present in the stabilizer compositions. Use of abietyl organophosphites of the present invention may result in enhanced polymer protection when added to polymer by reducing the formation of color resulting from the presence of the phenols. Such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate), di-N-octadecyl 3,5-di-tert-butyl-4-hydroxybenzyl-phosphonate, 1,3,5-tris(3,5-di-tert-butyl-4-hydroxybenzyl-)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6- di-9 oxaoctamethylene bis(3-methyl-5-tert-butyl-4-hydroxyhydrocinnamate), 2,6-di-tert-butyl-p-cresol,2,2'-ethylidene-bis (4,6-di-tertbutylphenol),1,3,5-tris-(2,6-di-methyl-4-tert-butyl-3-hydroxybenzyl) isocyanurate. 1,1,3-tris-(2-methyl-4-hydroxy-5-tert-butylphenyl)butane, 1,3,5-tris-(2-(3,5-di-tert-butyl-4-hydroxyhydrocinnamoyloxy)-ethyl)-isocyanurate, 3,5-di(3,5-di-tert-butyl-4-hydroxybenzyl)-mesitol, hexa-methylene bis(3,5-di-tert-butyl-4-hydroxyhydrocinnamate), 1-(3,5-ditert-butyl-4-hydroxyanilino)-3, 5-di(octylthio)-s-triazine, N,N'-hexamethylene-bis(3,5-di-tert-butyl-4-hydroxyhydro-cinnamamide), calcium bis (ethyl-3,5-di-tert-butyl-4-hydroxybenzylphosphonate), ethylene bis(3,3-di(3-tert-butyl-4-hydroxyphenyl)butyrate), octyl 3,5-di-tert-butyl-4-hydroxybenzylmercaptoacetate, bis(3,5-di-tert-butyl-4-hydroxyhydrocinnamoyl)hydrazide, and N,N'-bis-(2-(3,5-tert-butyl-4-hydroxyhydroxocinnamoyloxy)-ethyl)-oxamide, and preferably neopentanetetrayl tetrakis(3,5-di-tert-butyl-4-hydroxyhydrocinnamate), N-octadecyl 3,5-di-tert-butyl-4-hydroxyhydrocinnamate, 1,3,5-trimethyl-2,4,6-tris (3,5-di-tert-butyl-4-hydroxybenzyl)benzene, 1,3,5-tris-(3,5 di-tert-butyl-4-hydroxybenzyl)isocyanurate, 2,6-di-tert-butyl-p-cresol or 2,2'-ethylidene-bis(4,6-di-tert-butylphenol).

Other additives, such as oxazapholidines, may be present. Any or all of these additives might be used in combination with the materials of this invention in a polymer, without precombining with the phosphite and hindered amine blend.

Neutralizers may be added which are acid accepting products such as Ca, Zn, Mg, Al soaps of carboxylic acids, hydrotalcites, Ca, Mg, Zn, Al oxides or carbonates. Calcium stearate is a preferred neutralizer.

The compositions of the present invention may be substantially free of polymeric material outside of the group consisting of hindered piperidinyl light stabilizers and organic phosphite esters, for example, containing less than 10 percent by weight thereof based on the total weight of the composition, more preferably less than 5 percent by weight thereof and most preferably less than 1 percent by weight thereof, or may be totally free of polymeric materials such as those set out above for example containing 0 weight percent of polyvinyl chloride or polyolefins such as polypropylene.

The stabilizer composition of the present invention may find use when added to any of the polymers known in the art needing stabilization, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinylchloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the organic phosphite ester stabilizer compositions of the invention are particularly useful in stablizing thermoplastic polymers, such as polyolefins, polycarbonates, polyesters, polyphenylene ethers and styrenic polymers.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may have the organic phosphite ester compositions added thereto. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may use the present compositions. Also copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene/isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidenenorbornene may find the present composition useful; as well as mixtures of such copolymers and their mixtures with polymers mentioned above, for example polypropylene/ethylene-propylenecopolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butdiene, styrene/acrylonitrile, styrene/alkyl methacrylate, styrene/maleic anhydride, styrene/butadiene/ethylacrylate/styrene/acrylonitrile/methylacrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene styrene. Styrenic polymers may additionally or alternatively include graft copolymers of styrene or alphamethylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polyphers may also find the present compositions useful. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also find the present composition useful. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also find the present composition useful. These compositions include resins such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinylchloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride-isoprene copolymer, vinyl chloride-chlorinated propylene copolymer, vinyl chloride-vinylidene chloride-vinyl acetate tercopolymer, vinyl chloride-acrylic acid ester copolymers, vinylchloride-maleic acid ester copolymers, vinyl chloride-methacrylic acid ester copolymers, vinyl chloride-acrylonitrile copolymer and internally platicized polyvinyl chloride.

Other thermoplastic polymers which may incorporate the compositions include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1, 4-dimethylol-cyclohexane terephthalate, poly-2(2,2,-4(4-hydroxyphenyl)-propane) terphthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be use the present compositions.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The organic phosphite ester compositions of the present invention preferably contain 10 weight percent to 99.9 weight percent organic phosphite ester based on the total weight of the composition, more preferably from 80 weight percent to 99.9 weight percent thereof, and most preferably from 95 to 99 weight percent thereof; and preferably the compositions contain 0.1 weight percent to 90 weight percent hindered piperidinyl light stabilizer based on the total weight of the composition light stabilizer, more preferably from 0.1 weight percent to 20 weight thereof, and more preferably from 1 weight percent to 5 weight percent thereof.

Hindered amine light stabilizers are generally defined as compounds which are aliphatic amines or saturated cyclic amines which have no protons on two of the carbon atoms attached to nitrogen. They will form stable nitroxyl radicals.

EXAMPLES

The following examples illustrate the advantageous effect obtained by preparing compositions containing an organic phosphite ester and a hindered piperidinyl light stabilizer. The composition exhibit enhanced hydrolytic stability of the organic phosphite ester while containing both an antioxidant and a light stabilizer.

Example A is a control example which was bis 2,4-di-t-butylphenyl pentaerythritol diphosphite without any hindered piperidinyl light stabilizer therein. Example 1 is bis 2,4-di-t-butyl phenyl pentaerythritol disphosphite having admixed therewith 1.0 weight percent of poly-(N-B-hydroxyethyl-2,2,6,6-tetramethyl-4-hydroxy piperidinyl succinate) based on the total weight of the phosphite. Example 2 is bis 2,4-di-t-butyl phenyl pentaerythritol diphosphite having admixed therewith poly-((6-((1,1,3,3-tetramethylbutyl)-imino)-1,3,5-triazine 2,4-diyl(2-(2,2,6,6-tetramethyl piperidinyl)-iminohexamethylene) (4-2,2,6,6-tetramethyl piperidinyl)-imino)).

Samples 1 and 2 were prepared as follows:

For examples 1 and 2, 25 grams of 2,4-di-t-butyl phenyl pentaerythritol diphosphite was combined with 0.25 grams of the hindered piperidinyl light stabilizer and 20 ml of toluene, the solution was stirred for 30 minutes and then the toluene was stripped off at 40° C. at full pump vacuum until dry.

Phosphite products when exposed to a humid environment will absorb moisture and gain weight. This weight gain generally is followed by increases in acidity of the product. The increased acidity is measured by dissolving a weighed sample of product in methylene chloride and titrating with 0.02N sodium butoxide to a bromothymol blue end point. The acid number is calculated as follows:

$$\frac{\text{ml NaButoxide} \times \text{N NaButoxide} \times 56.1}{\text{Sample weight in grams}} = AN$$

The samples were placed in a chamber at 80% relative humidity and having ambient laboratory temperature (70° F.). AN means acid number, and is set out below as acid value.

TABLE 1

| | Acid Value (% Weight Gain) After Hours | | | | |
|---|---|---|---|---|---|
| Example | 0 Hours | 24 Hours | 48 Hours | 72 Hours | 144 Hours |
| A | 0.32 | 7.3 | 12.8 | 41 | >>50 |
|   |      | (0.8) | (2.5) | (5.8) | (20.7) |
| 1 | 0.36 | * | * | 7.4 | 39 |
|   |      | (0.0) | (0.18) | (0.62) | (6.0) |
| 2 | 1.09 | * | * | 8.2 | 48 |

TABLE 1-continued

| | Acid Value (% Weight Gain) After Hours | | | | |
|---|---|---|---|---|---|
| Example | 0 Hours | 24 Hours | 48 Hours | 72 Hours | 144 Hours |
| | | (0.04) | (0.22) | (0.78) | (6.85) |

*No acid number measurement taken for examples at 24–48 hrs. as weight gain was not substantial.

Note that examples 1 and 2 containing the hindered piperidinyl light stabilizers show significantly reduced hydrolysis as indicated by reduced acid numbers and percent weight gain.

What is claimed is:

1. An organo phosphite ester composition comprising:
   (a) organic phosphite ester present at a level of from 80 weight percent to 99.9 weight percent based on the total weight of the composition; and
   (b) a hindered piperidinyl light stabilizer in an amount sufficient to improve the hydrolytic stability of the phosphite ester, said piperidinyl light stabilizer being present at a level of from 0.1 weight percent to 20 weight percent based on the total weight of the composition.

2. The composition of claim 1 wherein said phosphite ester is selected from the group consisting of tris(nonylphenyl) phosphite, triphenyl phosphite, distearyl pentaerythritol diphosphite, bis(2,4,6-tri-t-butylphenyl) pentaerythritol diphosphite and bis (2,4-di-t-butylphenyl) pentaerythritol diphosphite.

3. The composition of claim 2 where said hindered piperidinyl light stabilizer is represented by the formula:

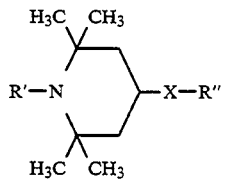

Wherein R″ and R′ are independently selected from hydrogen and functionalized hydrocarbons and X is selected from the group consisting of O and N.

4. The composition of claim 3 wherein said phosphite ester is bis(2,4-di-ti-butyl phenyl) pentaerythritol diphosphite.

5. The composition of claim 4 wherein said piperidinyl stabilizer is present at a level of from 0.1 weight percent to 5 weight percent based on the total weight of the composition.

6. The composition of claim 5 wherein said phosphite is present at a level of from 99.99 weight percent to 95 weight percent based on the total weight of the composition.

7. An organic phosphite ester composition consisting essentially of:
   (a) an organic phosphite ester present at a level of from 80 weight percent to 99.9 weight percent based on the total weight of the composition; and
   (b) an amount of a hindered piperdinyl light stabilizer sufficient to enhance the hydrolytic stability of said organic phosphite ester, said piperidinyl light stabilizer being present at a level of from 0.1 weight percent to 20 weight percent based on the total weight of the composition.

8. The composition of claim 1 consisting essentially of said organic phosphite ester and said hindered piperidinyl light stablizer.

9. The composition of claim 1 consisting of said organic phosphite ester and said hindered piperdyl light stablizer.

* * * * *

Adverse Decisions In Interference

Patent No. 5,342,978, William P. Enlow, Leo L. Valdiserri, ORGANIC PHOSPHITE ESTER COMPOSITIONS CONTAINING HINDERED PIPERDINYL LIGHT STABILIZERS, Interference No. 103,609, final judgment adverse to the patentees rendered February 23, 1998, as to claims 1-9.
*(Official Gazette June 2, 1998)*